United States Patent
Coppola et al.

(10) Patent No.: US 6,306,377 B1
(45) Date of Patent: Oct. 23, 2001

(54) HAIR STRAIGHTENING/SMOOTHING COMPOSITION

(75) Inventors: Linda S. Coppola, Stamford; Teresa Ferullo, Wilton, both of CT (US)

(73) Assignee: Shiseido Co., Ltd., Tokyo (JP)

( * ) Notice: Subject to any disclaimer, the term of this patent is extended or adjusted under 35 U.S.C. 154(b) by 0 days.

(21) Appl. No.: 09/237,266

(22) Filed: Jan. 25, 1999

Related U.S. Application Data

(60) Provisional application No. 60/073,057, filed on Jan. 29, 1998.

(51) Int. Cl.[7] ......................................................... A61K 7/06
(52) U.S. Cl. ......................................... 424/70.1; 424/70.2
(58) Field of Search ................................ 424/70.1, 70.11, 424/70.12, 70.19

(56) References Cited

U.S. PATENT DOCUMENTS 5,955,066 * 9/1999 Sako et al. ........................ 424/70.12

* cited by examiner

Primary Examiner—Shelley A. Dodson
(74) Attorney, Agent, or Firm—Melvin I. Stoltz

(57) ABSTRACT

By incorporating cationic guar gums in combination with nonionic guar gums in a single gel composition, a highly effective, hair straightening/smoothing composition is realized which achieves the temporary straightening and/or smoothing of hair fibers, without chemically interacting with the hair fiber itself. By employing the present invention, a temporary hair straightening effect is realized which enables a wide variety of hair styles or fashions to be attained, while still enabling the hair change effect to be easily reversed by merely washing the hair to remove the chemical formulation. In addition, the physical properties of the hair fibers, such as feel, shine, luster, softness and manageability are retained without adverse effect. In the preferred embodiment, in addition to employing a cationic guar gum, in combination with a nonionic guar gum, the present invention also incorporates additives such as humidity protectors, fragrances, preservatives, pH controllers, and water.

12 Claims, No Drawings

HAIR STRAIGHTENING/SMOOTHING COMPOSITION

This application claims priority from a provisional application No. 60/073,057 filed Jan. 29, 1998.

TECHNICAL FIELD

This invention relates to hair straightening and/or smoothing compositions and, more particularly to a hair straightening/smoothing composition which provides a temporary hair straightening effect, without chemically interacting with the hair fibers.

BACKGROUND ART

As is well known in the art, hair fibers are composed of a unique protein called "keratin" which is distinguished by the fact that it contains a very significant amount of an amino acid (cysteine) which contains the element sulfur in addition to the elements nitrogen, oxygen, carbon and hydrogen. In the natural synthesis of hair, the element sulfur covalently links intra or inter polypeptide chains (K) through two sulfur atoms (S-S) to give keratin protein (K-S-S-K). Only by chemical action can this covalent linkage be broken.

Since these disulfide bonds are relatively strong bonds and are not affected by water, permanent results are obtained by altering the disulfide bonds through cleavage and recombination. In this way, a permanent configuration change of the hair is attained. However, chemical action is required in order for this disulfide linkage to be broken. In this regard, many prior art compositions have been developed for permanent waving or straightening of hair which treat the hair with chemical agents to break the disulfide (cysteine) linkage in the hair while the hair is mechanically maintained in the desired configuration.

When a sufficient number of hair disulfide bonds have been broken, the hair is realigned to pair previously unpaired hair protein thiol groups opposite each other. At this point, the hair is rinsed to remove the first chemical reactant and then saturated with a second agent to reform the disulfide bonds between the newly paired hair protein thiols. This gives the hair a new configuration.

Although the chemicals employed in achieving either hair straightening or permanent hair waving provide excellent results, process problems exist which are difficult to control. One of the disadvantages is the fact that these processes must be conducted at elevated pH levels. However, since the skin surface of humans is usually at a weak acidic level, the use of products at elevated pH causes discomfort, irritation, and/or adverse reactions. Although low pH levels would be desirable, the permanent wave or straightening results produced at low pH levels are not satisfactory. Other disadvantages of prior art chemical agents are the irreversible fiber alteration made evident by increased fiber porosity and decreased tensile properties.

In the art of chemically altering hair fiber configurations, there is much trial and error, with the hair being over processed, in some instances. The characteristics of over-processing are raspy feel to the hair or a loss of natural underlying color. Structural evaluation of the hair fiber by instrumentation usually reveals that the structural integrity of the hair is lessened, which is evidenced by either an increase in the amount of cysteine and cysteic acid or a lessening of the cysteine content relative to the hair not so processed.

In view of the substantial damage that may be caused to hair fibers by employing chemicals for structurally altering the hair fiber configuration, increased interest has been paid to the development of chemicals and application techniques which achieve a hair configuration altering result which is on a temporary basis and does not cause a chemical hair fiber interaction. Although substantial effort has been expended in the prior art to achieve an effective composition capable of producing hair straightening on a temporary basis without adversely affecting the hair fiber itself, such attempts have failed to produce a viable composition, prior to the present invention.

DETAILED DESCRIPTION

By employing the present invention, the prior art difficulties and inabilities are overcome, and a highly effective, hair straightening/smoothing composition is realized which achieves the straightening and/or smoothing of hair fibers, without chemically interacting with the hair fiber itself. As a result, a temporary hair straightening effect is realized which enables a wide variety of hair styles or fashions to be attained, while still enabling the hair change effect to be easily reversed by merely washing the hair to remove the chemical formulation. As a result, the prior art drawbacks and inabilities are eliminated, and an effective hair straightening/smoothing composition is attained which allows the physical properties of the hair fibers, such as feel, shine, luster, softness and manageability to be retained without adverse effect.

In accordance with the present invention, the desirable and previously unattainable results are realized by employing a formulation incorporating cationic guar gums in combination with nonionic guar gums. By applying these two components to a head of hair, in the manner detailed below, the hair fibers are straightened and maintained in a straight configuration, until the chemical formulation is washed out of the hair.

In addition to employing a cationic guar gum, in combination with a nonionic guar gum, the preferred formulation of the present invention also incorporates additives for protecting the hair fibers from humidity. In this way, a non-chemical, temporary hair straightening/smoothing formulation is attained which redefines hair texture and imparts humidity protection thereto. Furthermore, the preferred formulation also incorporates additional additives selected from the group consisting of fragrances, preservatives, pH controllers, and water. By employing these compounds, a highly effective hair straightening/smoothing composition is realized which attains these desirable hair straightening/smoothing results without chemical interaction with the hair fibers.

In Table 1, an overall general formulation for the hair straightening/smoothing gel composition of the present invention is provided. By referring to this formulation, the various desired ingredients and quantity range for each ingredient is detailed as the percent by weight of each ingredient, based upon the weight of the entire composition.

TABLE I

HAIR STRAIGHTENING/SMOOTHING GEL COMPOSITION

| INGREDIENT | WEIGHT PERCENTAGE RANGE |
| --- | --- |
| Cationic Guar Gum | 0.25–1.50% |
| Nonionic Guar Gum | 0.25–0.75% |
| Fragrance | 0.01–0.50% |
| Preservative | 0.10–1.7% |

TABLE I-continued

HAIR STRAIGHTENING/SMOOTHING GEL COMPOSITION

| INGREDIENT | WEIGHT PERCENTAGE RANGE |
| --- | --- |
| pH Controller | 0.05–0.5% |
| Water | q.s. to 100% |

As is detailed in Table 1, the principal ingredients of the hair straightening/smoothing gel composition of the present invention comprises the combination of a nonionic guar gum and a cationic guar gum. Although any desired nonionic guar gum can be employed, the preferred nonionic guar gum comprises hydroxypropyl guar. Similarly, any desired cationic guar gum can be employed to form an effective hair straightening/smoothing gel. However, it has been found that the preferred cationic guar gum comprises guar hydroxypropyltrimonium chloride. In addition to these principal components, other ingredients preferably incorporated into the composition include one or more selected from the group consisting of fragrances, preservatives, pH controllers, and water.

The preferred formulation for the hair straightening/smoothing gel of the present invention also incorporates a humidity protecting agent. By incorporating a humidity protecting agent in the composition, substantially enhanced retention of straightened/smoothed hair is realized, since varying humidity levels have little or no effect on causing the natural curled hair configuration to return to washing of the entire head of hair. The preferred formulation incorporating a humidity protecting agent is detailed in Table II.

TABLE II

HAIR STRAIGHTENING/SMOOTHING GEL COMPOSITION

| INGREDIENT | WEIGHT PERCENTAGE RANGE |
| --- | --- |
| Nonionic Guar Gum | 0.25–1.50% |
| Cationic Guar Gum | 0.25–0.75% |
| Humidity Protecting Agent | 0.05–5.00% |
| Fragrance | 0.01–0.50% |
| Preservative | 0.10–1.7% |
| pH Controller | 0.05–0.5% |
| Water | q.s. to 100% |

Although any desired humidity protecting agent can be incorporated into the hair gel composition of this invention, the preferred agent is selected from the group consisting of hydrolyzed wheat protein, hydrolyzed wheat starch, and an aminofunctional silicone. In addition, the preferred aminofunctional silicone comprises trimethylsilyamodimethicone. By employing one or more humidity protecting agents in combination with the cationic guar gum and the nonionic guar gum, a highly effective, long lasting hair straightening/smoothing gel is realized.

In Tables III and IV, further detailed formulations for the straightening/smoothing gel are provided, specifically defining preferred compositions of the gel formulation with a humidity protecting agent incorporated therein. In each of these formulations, as well as the formulations defined in Tables I and II, the other additives are included.

TABLE III

HAIR STRAIGHTENING/SMOOTHING GEL COMPOSITION

| INGREDIENT | WEIGHT PERCENTAGE RANGE |
| --- | --- |
| Guar Hydroxypropyltrimonium chloride | 0.25–1.50% |
| Hydroxypropyl guar | 0.25–0.75% |
| Hydrolyzed Wheat Protein, Hydrolyzed Wheat Starch and/or Trimethylsilylamodimethicone | 0.05–5.00% |
| Fragrance | 0.01–0.50% |
| Preservative | 0.10–1.7% |
| pH Controller | 0.05–0.5% |
| Water | q.s. to 10% |

TABLE IV

HAIR STRAIGHTENING/SMOOTHING GEL COMPOSITION

| INGREDIENT | WEIGHT PERCENTAGE RANGE |
| --- | --- |
| Guar Hydroxypropyltrimonium chloride | 0.25–1.50% |
| Hydroxypropyl guar | 0.25–0.75% |
| Trimethylsilylamodimethicone | 0.05–3.00% |
| Hydrolyzed Wheat Protein, Hydrolyzed Wheat Starch | 0.05–5.00% |
| Fragrance | 0.01–0.50% |
| Preservative | 0.10–1.7% |
| pH Controller | 0.05–0.5% |
| Water | q.s. to 10% |

It has been found that the preferred preservative is selected from the group consisting of diazolidinyl urea, methylparaben, and propylparaben. In addition, the preferred pH controller comprises citric acid, although other pH controlling agents can be employed with equal efficacy.

By employing the formulations detailed above, a hair straightening/smoothing gel is achieved that is capable of virtually eliminating curls and/or frizziness, leaving the hair more manageable and stylable. Hair texture is attained with the use of these compositions, controlling the hair at all humidity levels. By using this invention, added flexibility, conditioning, and high shine are achieved.

By combining a cationic guar gum and a nonionic guar gum as the principal constituents of the gel formulation of the present invention, the desired hair straightening/smoothing is realized. It is believed that the weight of the gums change the configuration of the hair from curly to straight, when the gel is combed through the hair fibers. As the hair dries, the gums form a film over each hair fiber, maintaining each hair strand substantially straight, smooth, and frizzy free. By employing heat as the final step in the application process, the new configuration is set in the hair, enabling the hair to remain straight and smooth until washed.

As discussed above, humidity protecting agents are preferably incorporated into the hair straightening/smoothing gel of the present invention to impart added humidity protection to the hair fibers. It has been found that by employing humidity protecting agents selected from the group consisting of hydrolyzed wheat protein and hydrolyzed wheat starch, a film is formed over the hair which protects the hair fibers from moisture. Furthermore, the incorporation of an aminofunctional silicone, either as an addition to the humidity protecting agent or as the sole humidity protecting agent, a formulation is realized which attaches itself to the hair and repels water. This is achieved by having the silicone uniformly deposited on the hair fiber, penetrating the cuticle due to its small particle size. In this way, the hair fiber is sealed and moisture is repelled.

In the preferred application process, the head of hair is shampooed and then divided into sections while still damp. The hair straightening/smoothing gel composition of the present invention is then generously applied to the hair fibers. The gel is then combed through the hair fibers from the roots to the ends of the hair fibers. Once fully applied throughout the entire head of hair, the hair is dried with heat.

By employing the formulations detailed above and applying these formulations in the manner described herein, the desired hair straightening and smoothing is attained on a temporary basis, enabling individuals to achieve alternate styles of hair configurations while not requiring chemical interaction of the hair fibers themselves. As a result, all of the difficulties presently existing in the prior art are eliminated and a highly effective, temporary hair straightening and smoothing composition is realized.

The invention accordingly comprises the several steps and the relation of one or more of such steps with respect to each of the others, and the composition possessing the features, properties and relation of components, all as exemplified herein, with the scope of the invention being indicated in the claims.

BEST MODE FOR CARRYING OUT THE INVENTION

In order to substantiate the efficacy of creating a hair straightening/smoothing gel formulation of the present invention, a plurality of alternate compositions manufactured in accordance with the present invention were created and tested as detailed below. The following examples are presented in order to fully demonstrate the highly effective hair straightening/smoothing results attained.

By reviewing the following examples, the ability of the gel composition of the present invention to produce the desired temporary hair straightening and smoothing result is clearly established. However, it is to be understood that the following examples are intended as teaching the best mode for carrying out the present invention and are not intended to limit the breadth of this discovery.

In order to prove the efficacy of the preferred formulation of the present invention, the following comparative tests were conducted using alternate gel formulations. In conducting these tests, two grams of naturally curly brown hair were selected and washed with a shampoo formulated for normal hair. Each hair strand was shampooed for 30 seconds using one milliliter of shampoo and then rinsed for one minute. Thereafter, 16 hair strands were selected and separated into four groups.

The gel formulation defined in Table V, along with two variations thereof, as detailed below, were created, and one formulation was applied to all of the hair strands in one group. The fourth group remained untreated for comparative purposes.

The treated hair strands had the particular gel product applied to the damp hair strands in the manner detailed above. Then, the top of each hair strand was placed in a vice and blown dry using a brush to pull the hair strands straight. This procedure was followed for each of the hair strands, whether or not the gel composition was applied to the hair strand.

When the hair strands were fully dry and straight, the strands were hung on a ruled plastic board with clips and the initial length of each hair strand was recorded. The plastic ruled board and hair strands were then placed in a GS Blue Electric Controlled Relative Humidity Chamber, with the relative humidity set at 93%. Thereafter, the length of each hair strand was recorded at 15 minute intervals for the first hour and then recorded at each one-hour interval. After two hours total, no further change in length was noted and recordings were terminated.

This test procedure was employed to determine the efficacy of the gel formulation of the present invention to repel water absorption into the hair fibers due to humidity. The results of this test program are detailed in Table VI, wherein the overall percent change in length for each group of hair strands having each treatment are provided. In order to establish the percent change in length, the following formula was employed:

$$\% \text{ Change in Length} = \frac{\text{Initial Length} - \text{Interval Length}}{\text{Interval Length}}$$

In conducting the foregoing test, the preferred formulation for the hair straightening/smoothing gel composition of the present invention was employed, as detailed in Table V. For comparative purposes, in addition to the sample of untreated hair, a substantially identical formulation was employed, except silicone was deleted. In the final formulation, the silicone humidity protector was included and the hydrolyzed wheat protein and hydrolyzed wheat starch were deleted. In each instance, water was substituted for the missing ingredients.

TABLE V

| PREFERRED HAIR STRAIGHTENING/SMOOTHING GEL COMPOSITION | | |
|---|---|---|
| INGREDIENT | FUNCTION | WEIGHT % |
| Guar Hydroxypropyltrimonium Chloride | Cationic Guar Polymer | 1.230 |
| Hydroxypropyl Guar | Nonionic Guar Polymer | 0.520 |
| Trimethylsilylamodimethicone (and) Octoxynl-40 (and) Isolaureth-6 (and) glycerin | Silicone (Humidity Resistor) | 0.500 |
| Hydrolyzed Wheat Protein (and) Hydrolyzed Wheat Starch | Humidity Resistor | 0.250 |
| Methylparaben | Preservative | 0.100 |
| Propylene Glycol (and) Diazolidinyl Urea (and) Methylparaben (and) Propylparaben | Preservative | 0.100 |

TABLE V-continued

PREFERRED HAIR STRAIGHTENING/SMOOTHING GEL COMPOSITION

| INGREDIENT | FUNCTION | WEIGHT % |
|---|---|---|
| Fragrance | Fragrance | 0.075 |
| Water | | q.s. to 100% |

TABLE VI

HUMIDITY TESTING RESULTS
% Change in Hair Length when Exposed to 93% Relative humidity

| Time exposed to 93% Relative Humidity | Untreated | Treated with Formula of Table V | Treated With Formula of Table V with Hydrolyzed Wheat Protein and Hydrolyzed Wheat Starch Deleted | Treated with Formula of Table V with Silicone Deleted |
|---|---|---|---|---|
| 15 Minutes | 8.46% | 1.37% | 2.07% | 3.94% |
| 30 Minutes | 10.46% | 1.37% | 3.46% | 4.65% |
| 45 Minutes | 13.74% | 3.40% | 4.06% | 6.65% |
| 1 Hour | 14.38% | 4.06% | 5.45% | 7.30% |
| 2 Hours | 15.01% | 4.06% | 6.70% | 7.30% |

As is evident from a review of the results attained and detailed in Table VI, the hair straightening/smoothing gel of the present invention, as defined in Table V, achieved a highly effective, humidity resistant straightening of the hair fibers to which the gel composition was applied. As shown in the data provided, hair fibers treated with this preferred formulation experienced only a 4% reduction in length after two hours of exposure of 93% relative humidity. The untreated hair fibers experienced a 15% reduction in length during the same period of time.

Furthermore, as shown by the data in Table VI, the incorporation of the silicone compound or the hydrolyzed wheat protein and hydrolyzed wheat starch did not provide substantial humidity protection to the hair fibers. However, the inclusion of both compounds was the most effective. As the data shows, the silicone compound was incorporated into the formulation, without the incorporation of the hydrolyzed wheat protein and hydrolyzed wheat starch, a 6.7% overall reduction in length was realized, while the elimination of the silicone and the inclusion of the hydrolyzed wheat protein and hydrolyzed wheat starch achieved a 7.3% reduction in hair length at the end of the two hours.

As is evident from this data, all three formulations provide a highly effective hair straightening/smoothing composition capable of achieving the desired results for attaining added hair styling capabilities on a temporary basis. Furthermore, as detailed above, all of these hair straightening and smoothing results are achieved without chemically altering or interacting with the hair fibers, thereby preventing damage to the hair fibers.

In order to further demonstrate the efficacy of the present invention, numerous additional tests were conducted employing formulations manufactured in accordance with the present invention, with conventional prior art formulations employed as a comparative control. In Table VII, the formulations of each of these additional hair straightening/smoothing gel compositions are fully detailed. As is evident from a review of Table VII, the range of the preferred ingredients detailed above were tested, with their efficacy being detailed below.

TABLE VII

HAIR STRAIGHTENING/SMOOTHING GEL COMPOSITION

| Test Formulation | A | B | C | D | E | F | G |
|---|---|---|---|---|---|---|---|
| Cationic Gum | .5 | .75 | .75 | .75 | .75 | 1.12 | 1.23 |
| Nonionic Gum | .5 | .25 | .25 | .25 | .25 | 0.38 | 0.52 |
| Silicone | 0 | 0 | .50 | .50 | .50 | .50 | .50 |
| Cropeptide W | 0 | 0 | .25 | .25 | .25 | .25 | .25 |

Control #1: Rusk STR8 Manufactured by of
Control #2: Phytodefrisant Manufactured by of In each of the tests conducted in this series of experiments, the hair straightening and smoothing compositions detailed in Table VII were independently applied to test subjects having natural curly hair and having hair curled by permanent waving. In each of the tests, the full head of hair of the test subjects was shampooed with a conventional, daily, hair shampoo followed by a thorough rinsing of the head of hair. Thereafter, one formulation was applied to one-half of the head hair while a second formulation was applied to the other half of the head of hair.

In each instance, the particular formulation was applied to a fine-toothed comb and the comb was thoroughly worked through the hair from the roots to the ends. In order to assure total coverage of the hair with the desired formulation, the head of hair was combed in small sections. Once the desired formulations were thoroughly applied to the hair, the entire head of hair was dried in the usual manner.

Once the application process was completed, the results achieved from the application of each hair straightening/smoothing gel composition was evaluated. In this regard, the stylist evaluated each product for feel, spread-ability, application ease, penetration, wet and dry combability, tackiness, manageability, fragrance, body-hold, dry-feel, curl reduction, flaking, luster, and static.

As a result of these extensive test evaluations, it was found that Formulations A through G were all preferred over the two commercially available products employed as controls. In addition, although it was found that Formulation A provided superior results to each of the control formulations, Formulations G was judged as having the best overall performance as a temporary hair straightening/smoothing gel and was preferred over the other formulations. However, although Formulation G was shown to provide the best results in comparison to the other test formulations, the results of these extensive test procedures clearly demonstrated that each of the hair straightening/smoothing gel formulations manufactured in accordance with the present invention provided superior performance when compared to conventional, commercially available hair straightening/smoothing products.

It will thus be seen that the objects set forth above, among those made apparent from the preceding description, are efficiently attained and, since certain changes may be made in carrying out the above method and in the compositions set forth, without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Particularly, it is to be understood that in said claims, ingredients or compounds recited in the singular are intended to include compatible mixtures of such ingredients whenever the sense permits.

Having described our invention, what we claims as new and desire to secure by Letters Patent is:

1. A hair straightening and smoothing gel composition for temporarily achieving straightening and smoothing of hair fibers comprising an aqueous formulation incorporating cationic guar gums in combination with nonionic guar gums.

2. The hair straightening/smoothing gel composition defined in claim 1, and further comprising one or more additives selected from the group consisting of humidity protecting agents, fragrances, preservatives, and pH controllers.

3. A hair straightening and smoothing gel composition for temporarily straightening and smoothing hair fibers comprising:
   A. between about 0.25% and 1.50% by weight based upon the weight of the entire composition of a cationic guar gum;
   B. between about 0.25% and 0.75% by weight based upon the weight of the entire composition of a nonionic guar gum; and
   C. water forming the balance.

4. The hair straightening/smoothing gel composition defined in claim 3, wherein the nonionic guar gum comprises hydroxypropyl guar.

5. The hair straightening/smoothing gel composition defined in claim 4, wherein the cationic guar gum comprises guar hydroxypropyltrimonium chloride.

6. The hair straightening/smoothing gel composition defined in claim 3, and further comprising one or more additives selected from the group consisting of humidity protecting agents, fragrances, preservatives, and pH controllers.

7. The hair straightening/smoothing gel composition defined in claim 6, wherein said composition is further defined as comprising:
   D. between about 0.05% by weight and 5.0% by weight of the weight of a humidity protecting agent;
   E. between about 0.01% by weight and 0.50% by weight of the weight of a fragrance;
   F. between about 0.10% by weight and 1.7% by weight of the weight of a preservative; and
   G. between about 0.05% by weight and 0.5% by weight of the weight of a pH controller.

8. The hair straightening/smoothing gel composition defined in claim 7, wherein said humidity protecting agent is further defined as comprising at least one selected from the group consisting of hydrolyzed wheat protein, hydrolyzed wheat starch, and an aminofunctional silicone.

9. The hair straightening/smoothing gel composition defined in claim 8, wherein the aminofunctional silicone is further defined as comprising trimethylsilyamodimethicone.

10. The hair straightening/smoothing gel composition defined in claim 7, wherein the preservative is further defined as comprising one selected from the group consisting of diazolidinyl urea, methylparaben, and propylparaben.

11. The hair straightening/smoothing gel composition defined in claim 7, wherein the pH controller comprises citric acid.

12. A hair straightening and smoothing gel composition for temporarily straightening and smoothing hair fibers comprising:
   A. about 1.23% by weight based upon the weight of the entire composition of guar hydroxypropyltimonium chloride;
   B. about 0.52% by weight based upon the weight of the entire composition of hydroxypropyl guar;
   C. about 0.50% by weight based upon the weight of the entire composition of trimethylsilylamodimethicone and octoxynol-40 and isolaureth-6 and glycerin;
   D. about 0.25% by weight based upon the weight of the entire composition of hydrolyzed wheat protein and hydrolyzed wheat starch;
   E. about 0.10% by weight based upon the weight of the entire composition of methylparaben;
   F. about 1.0% by weight based upon the weight of the entire composition of propylene glycol and diazolidinyl urea and methylparaben and propylparaben;
   G. about 0.075% by weight based upon the weight of the entire composition of fragrance; and
   H. water forming the balance.

* * * * *